(12) United States Patent
Nielsen et al.

(10) Patent No.: US 8,795,258 B2
(45) Date of Patent: Aug. 5, 2014

(54) URISHEATH WITH MOULDED UNROLLING STRIP

(75) Inventors: Henrik Lindenskov Nielsen, Smoerum (DK); Johan Christiansson, Hoerby (SE); Peter Persson, Hoerby (SE)

(73) Assignee: Coloplast A/S (DK)

( * ) Notice: Subject to any disclaimer, the term of this patent is extended or adjusted under 35 U.S.C. 154(b) by 842 days.

(21) Appl. No.: 12/281,219

(22) PCT Filed: Feb. 28, 2007

(86) PCT No.: PCT/EP2007/051916
§ 371 (c)(1),
(2), (4) Date: Sep. 22, 2008

(87) PCT Pub. No.: WO2007/099129
PCT Pub. Date: Sep. 7, 2007

(65) Prior Publication Data
US 2009/0018530 A1    Jan. 15, 2009

Related U.S. Application Data

(60) Provisional application No. 60/794,119, filed on Apr. 24, 2006.

(30) Foreign Application Priority Data

Mar. 1, 2006  (DK) .................................. 2006 00297

(51) Int. Cl.
*A61M 27/00*    (2006.01)

(52) U.S. Cl.
USPC ........... 604/544; 604/327; 604/328; 604/329; 604/330; 604/331; 604/346; 604/347; 604/348; 604/349; 604/350; 604/351; 604/352; 604/353; 604/354; 604/317; 604/318; 604/319; 604/320; 604/321; 604/322; 604/323; 604/324; 604/325; 604/326; 604/364; 156/164; 156/566; 156/301; 156/292; 156/291; 156/298; 156/299; 156/300; 156/302; 156/324

(58) Field of Classification Search
USPC .......................................... 604/544, 327–331
See application file for complete search history.

(56) References Cited

U.S. PATENT DOCUMENTS 3,608,552 A    9/1971 Broerman
3,835,857 A    9/1974 Rogers, III et al.
(Continued)

FOREIGN PATENT DOCUMENTS

EP    162037 A2    11/1985
EP    710535 A1    5/1996
(Continued)

OTHER PUBLICATIONS

International Search Report.
(Continued)

*Primary Examiner* — Tatyana Zalukaeva
*Assistant Examiner* — Ilya Treyger
(74) *Attorney, Agent, or Firm* — Martin & Ferraro, LLP

(57) ABSTRACT

The urisheath provided here includes an element of thin material (a strip) that allows at least two lengths of it to run in a parallel fashion down either side of the sheath. The is obtained by injection molding the strip in liquid silicone in the silicone injection molding process for the urisheath, either by one, two or more component injection molding. The injection molding takes place in an injection molding form for a urisheath with a cavity for the body portion and a cavity for the strip portion wherein the cavity for the body portion is connected to the cavity for the strip portion creating an attachment zone between the strip and the sheath.

28 Claims, 5 Drawing Sheets

(56) References Cited

U.S. PATENT DOCUMENTS

Figure 1:
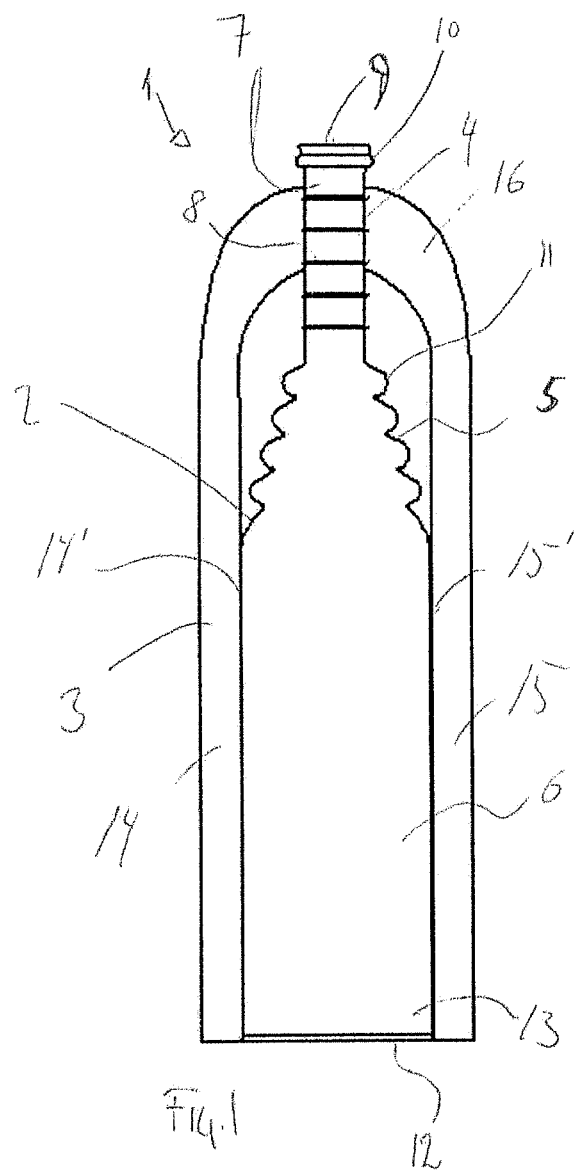

| | | | |
|---|---|---|---|
| 3,901,965 A | 8/1975 | Honeyman | |
| 4,149,695 A | 4/1979 | Quick et al. | |
| 4,581,026 A | 4/1986 | Schneider | |
| 4,594,761 A | 6/1986 | Murphy et al. | |
| 4,732,724 A | 3/1988 | Sterner | |
| 4,734,241 A | 3/1988 | Gerow | |
| 4,872,463 A * | 10/1989 | Nishizono | 128/844 |
| 4,934,382 A * | 6/1990 | Barone, Jr. | 128/844 |
| 5,554,141 A | 9/1996 | Wendler | |
| 5,685,870 A | 11/1997 | Tanghoj | |
| 5,713,880 A | 2/1998 | Anderson | |
| 6,250,303 B1 | 6/2001 | Delaney | |
| 6,376,432 B1 | 4/2002 | Leslie et al. | |
| 6,726,363 B1 | 4/2004 | Marbler | |
| 6,805,690 B2 * | 10/2004 | Ogden et al. | 604/352 |
| 2005/0101923 A1 | 5/2005 | Elson et al. | |
| 2008/0215021 A1 | 9/2008 | Cisko Jr. et al. | |
| 2009/0118688 A1 | 5/2009 | Nielsen et al. | |
| 2011/0118685 A1 | 5/2011 | Nielsen et al. | |
| 2011/0257615 A1 | 10/2011 | Nielsen et al. | |

FOREIGN PATENT DOCUMENTS

| | | | |
|---|---|---|---|
| EP | 979718 A1 | 2/2000 | |
| EP | 1 063 007 A1 | 12/2000 | |
| FR | 2 374 754 | 12/1996 | |
| FR | 2771923 | 6/1999 | |
| GB | 2 357 725 | 7/2001 | |
| IT | WO 97/40790 | * 11/1997 | |
| JP | 57-209051 A | 12/1982 | |
| JP | 58-001445 A | 1/1983 | |
| JP | 58001529 A | 1/1983 | |
| JP | 60-229716 A | 11/1985 | |
| JP | 61/277419 A | 12/1986 | |
| JP | 62-070012 A1 | 3/1987 | |
| JP | 01 110116 A | 4/1989 | |
| JP | 3-33617 U | 4/1991 | |
| JP | 4-19117 | 1/1992 | |
| JP | 5-506381 A | 9/1993 | |
| JP | 7-002019 U | 1/1995 | |
| JP | 8-336842 A | 12/1996 | |
| JP | 10183162 A | 7/1998 | |
| JP | 10-291235 A | 11/1998 | |
| JP | 2002-102110 A | 4/2002 | |
| JP | 2003-211500 A | 7/2003 | |
| JP | 2008-511360 A | 4/2008 | |
| JP | 2008-543423 A | 12/2008 | |
| WO | WO 91/17728 A1 | 11/1991 | |
| WO | WO 92/08426 A1 | 5/1992 | |
| WO | WO 93/03697 A1 | 3/1993 | |
| WO | WO-97/40790 | 11/1997 | |
| WO | WO-98/22275 | 5/1998 | |
| WO | WO 02/053070 A1 | 7/2002 | |
| WO | WO 2004/004796 A1 | 1/2004 | |
| WO | WO 2006/024637 | 3/2006 | |
| WO | WO 2007/040441 | 4/2007 | |
| WO | WO 2007/099129 | 9/2007 | |

OTHER PUBLICATIONS

English Translation of Japanese Office Action dated Jan. 5, 2012 for JP Application No. 2008-556777.

G. Steinbichler, "Spritzgeissen VonFluessigsiliconkautschuk", Kunststoffe, Carl Hanser Verlag, Muenchen, Germany, XP001176509, vol. 77, No. 10, pp. 931-933 (Oct. 1, 1997).

* cited by examiner

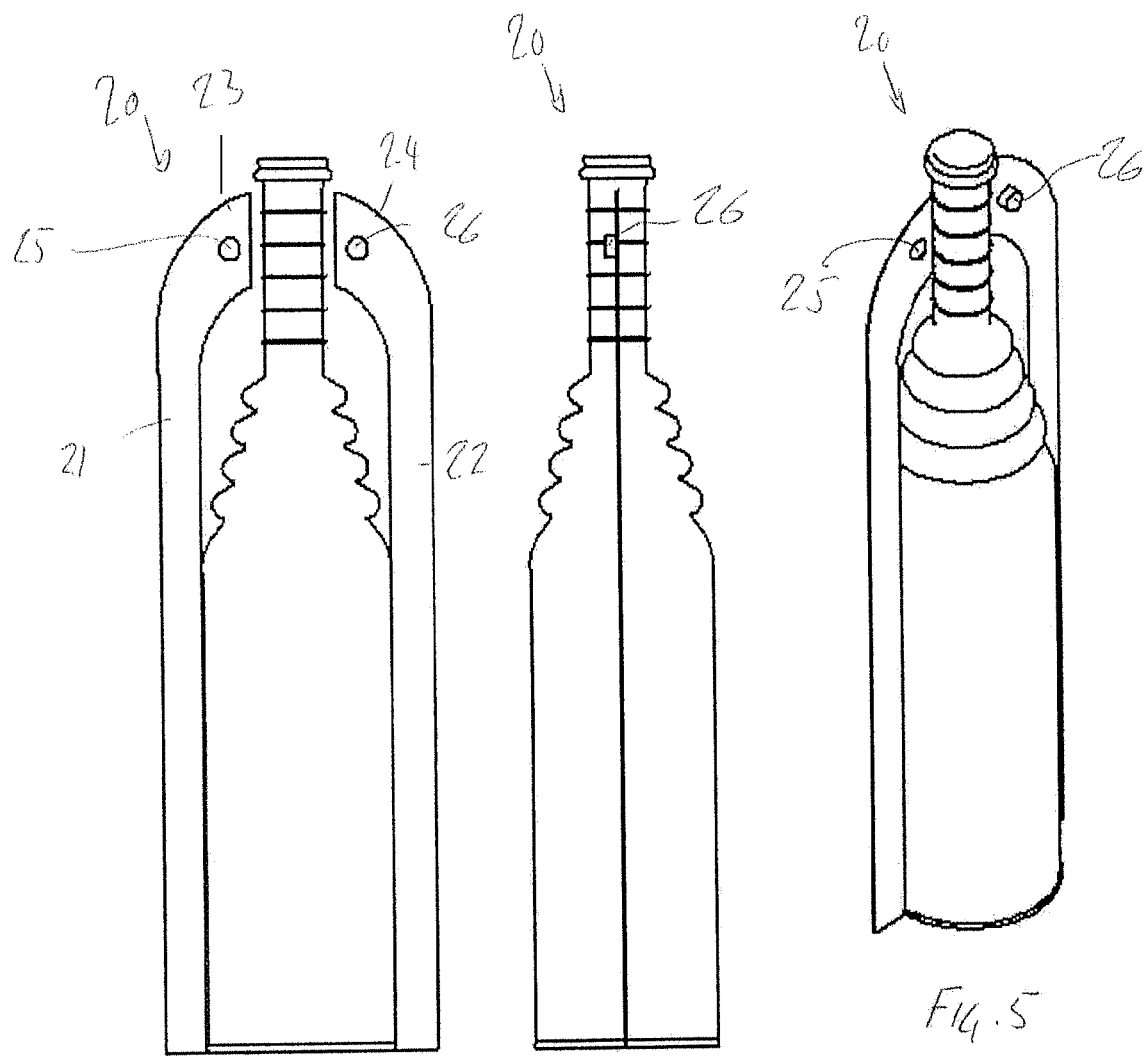

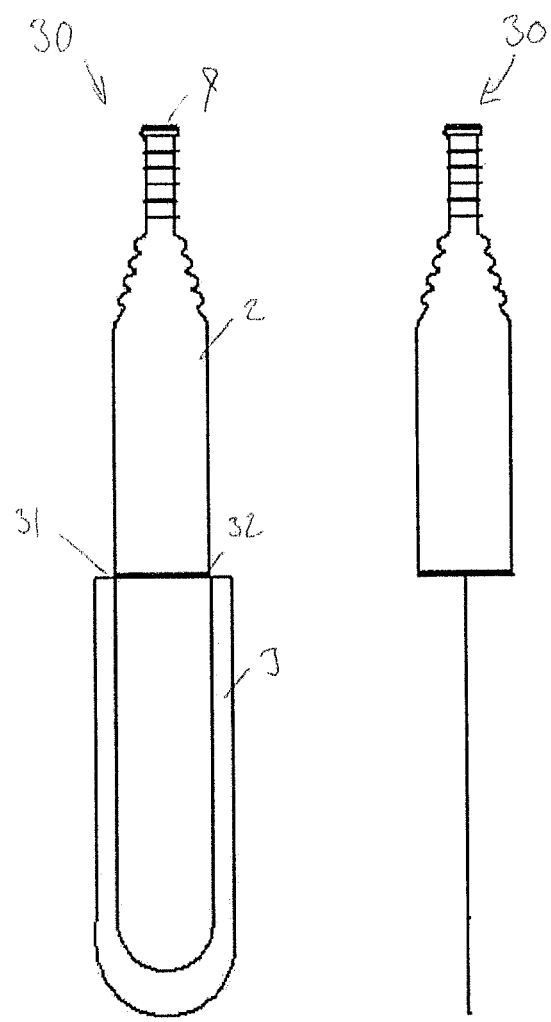

URISHEATH WITH MOULDED UNROLLING STRIP

BACKGROUND

External urinary catheters, also known as urisheaths, are conventionally used in urinary catheter devices for aiding male urinary incontinence and for use in hospitals in connection with treatment and surgery of urethral disorders. Such an external urinary catheter normally comprises a sheath or body portion enclosing the shaft of the penis, and a tip portion that is provided with a comparatively short discharge tube, which via a tube is connected to a urine collection bag that is e.g. fastened to the bed or the leg of the user. Unrolling a sheath correctly on a penis can be very challenging. This procedure is often performed by users with poor dexterity or by hospital staff wearing protective gloves for hygienic reasons. However, it is essential that the sheath be fitted correctly to ensure a leak proof seal between the skin and the sheath. Problems occur if the sheath does not unroll evenly or if the protective gloves stick to the sheath adhesive.

One present solution to this problem is a single strip assisting application of the sheath. However, this strip pulls only on one side of the sheath, which causes uneven roll and is difficult to hold with poor dexterity.

By using an injection-molding machine, the wall thickness of the product may be controlled very precisely by the design of the cavity of the injection-molding machine. Thus, a thin-walled product of high quality can be produced by this method.

SUMMARY

The solution to the problem of unrolling a urisheath provided here thus includes an element of thin material that allows at least two lengths of it to run in a parallel fashion down either side of the sheath. The two lengths of the element, the strips, are rolled with the sheath. The top end of the element towards the sheath tip is preferably formed as a loop big enough to grab and pull with a male thumb (the handle). When pulling the loop in a downward motion (that is from the sheath tip towards the opposite end of the sheath), the sheath is unrolled evenly. With the double action strip, the sheath is more easily unrolled onto the penis in an even fashion and without having to touch the adhesive. However, attaching this strip to the product is difficult and is done manually by very skilled operators. This manual operation is very costly. Automation of this process is considered also to be very costly too.

The solution to this problem is to injection mould the strip in liquid silicone in the silicone injection moulding process for the urisheath, either by one, two or more component injection moulding.

DETAILED DISCLOSURE

One aspect of the invention relates to a urisheath semi-manufacture product comprising a body portion and a strip portion wherein the strip portion is attached to the body portion in an attachment zone. The body portion extends from the urine outlet (a tip part) and an open end. The tip part is where the urine leaves the urisheath. This is preferably a comparatively short discharge tube. To this discharge tube, a drainage tube is often attached. The other end of the drainage tube is typically connected to a urine collection bag.

The attachment zone may be provided in a number of different ways; such as for example being formed as weakened zones, having lower tear strength than the strip portion and the urisheath respectively. Such weakened zones are typically formed of the same material as the strip portion and the urisheath, and having a smaller thickness than the strip portion and the urisheath.

Thus, when pulling the strip portion and the urisheath away from each other they will advantageously separate at the attachment zone.

Further alternative attachment zones may be provided by for example different types of materials having a tear strength which is smaller than that of the material of the strip portion and the material of the urisheath. Two-component injection moulding will produce such products.

The urisheath preferably further comprises adhesive on the inside to attach and seal to the penis. The urisheath preferably further comprises a flexible zone between the tip part and the body portion.

Figure 2:
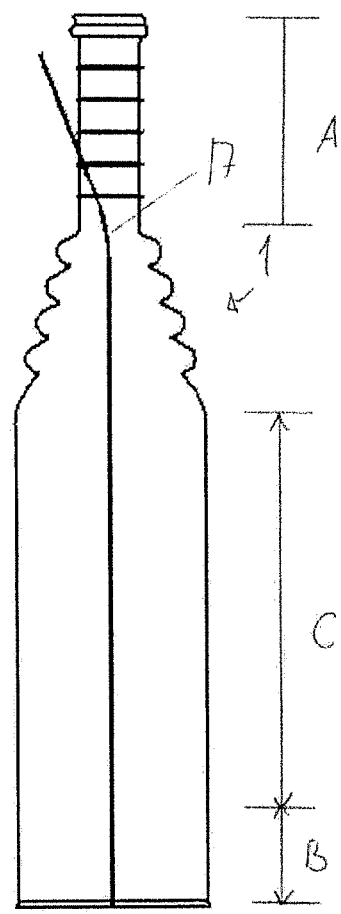

The tip part can be the top 3 cm of the entire urisheath (A on FIG. 2). Preferably that is ⅓ of the entire length of the urisheath (not including optional flexible zones). The root part of the urisheath is the part of the urisheath extending from the open end to ⅓ of the entire body portion (B on FIG. 2). The section between the tip portion and the root portion (excluding optional flexible zones) is referred to as the centred part (C on FIG. 2).

Such urisheath is injection moulded with an injection moulding form for a urisheath comprising a body portion and a strip portion, the form comprising a cavity for the body portion and a cavity for the strip portion wherein the cavity for the body portion is connected to the cavity for the strip portion. This form preferably comprises three parts: a core part, an upper shield part and a lower shield part.

In one embodiment, the strip portion comprises one strip. One strip is sufficient to unroll the urisheath on the penis. In another embodiment, the strip portion comprises two strips. Having two strips, preferably at opposite sides of a tubular urisheath, an even draw when applying the urisheath is obtained.

Such urisheath is injected moulded with an injection moulding form wherein the cavity for the strip portion comprises one strip. Alternatively, the cavity for the strip portion comprises two strips. The form with cavities for two strips preferably comprises these cavities diagonally across from each other, that are in the dividing line between the two shield parts.

It is troublesome to connect and align a strip on the urisheath before rolling the urisheath in a ready-to-use configuration. In one aspect of the present invention, the strip portion is attached to the body portion at the root part and at the tip part. That is, if there are two strips, each strip is attached to the body portion at the root part and at the tip part of the urisheath. Whether a continuous attachment or a point-like attachment, the strip will be oriented along the longitudinal direction of the urisheath. Hence easy connection and alignment of the strip(s) on the urisheath before rolling the urisheath in a ready-to-use configuration is obtained.

Such a urisheath is injected moulded with an injection moulding form wherein the connection between the cavity for the strip portion and the cavity for the body portion is at the root part.

The user will experience the attachment zones as resistance during the application of the urisheath. Thus, the balance between easy rolling of the urisheath during production on the one side, and the degree of resistance offered to the user on the other. In one embodiment, the strip portion is attached to the body portion at the root part, the centred part and at the tip part. In another embodiment, the strip portion is attached to the body portion along the entire centred portion. In yet another embodiment, the strip portion is attached to the body portion along the entire root- and centred portions and with a point like attachment to the tip portion.

Such a urisheath is injected moulded with an injection moulding form wherein the connections between the cavity for the body portion and the cavity for the strip portion are wider (in the urisheath longitudinal direction). That is, one form wherein there are connections between the cavity for the body portion and the cavity for the strip portion at the root part, the centred part and at the tip part. In another form, there is a connection between the cavity for the body portion and the cavity for the strip portion along the entire centred portion. In yet another moulding form, there is a connection between the cavity for the body portion and the cavity for the strip portion along the entire root- and centred portions and with a point like connection at the tip portion.

In a preferred embodiment, the attachment zone(s) between the body portion and the strip portion has lower tear strength than the body portion and the strip portion. Hence the result obtained is that when pulling the strip portion, the strip portion is detached from the body portion without destroying either the body portion or the strip portion.

Such a urisheath is injected moulded with an injection moulding form wherein the connection between the cavity for the body portion and the cavity for the strip portion is sufficiently thin, so that the mass of the material to be broken is small, that is the material in the attachment zone is thin.

In an alternative embodiment, the attachment zones are broken, e.g. cut, just before rolling the urisheath. One example is a continuous detachment and rolling process.

In the design of certain moulding forms, it is troublesome to join the two strips along side the urisheath. Thus, in one embodiment of the invention, the strip portion comprises two strips with attachment means for joining the two strips at the tip part of the strips.

Such a urisheath is injected moulded with an injection moulding form wherein each of the cavities for the strips comprises indentations providing attachment means for joining the two strips. An example of such attachment means is a hole in one strip and a hook on the other strip.

An alternative embodiment thereof, a separate handle is attached to the two strips after injection moulding.

In one embodiment of the invention, at least two strips are joined outside the rolled tubular section. This provides for one major advantage of the present invention: for example urisheath users with poor dexterity will now be able to apply the urisheath themselves, without outside help by only using one hand. This is a major break-through to the self-esteem of these users. In a further embodiment joint strips form a handle for unrolling the rolled tubular section. In an even further embodiment the joint strips form a finger-pull-hole. Such finger-pull-hole enables the user of for example an urisheath to insert a finger, and pull. Whereas an ear handle requires two fingers, and force between those, (tweezers grip), the ring only requires a pull force. Thus, it is preferred that the strip portion comprises two strips and further comprises a handle connecting the two strips. Preferably, the handle is thicker than the strips.

In one embodiment, the handle is positioned below the urisheath (see FIGS. 6 and 7), i.e. the strips extend from the root part in a direction away from the tip part. This position of the handle is preferably secured through the attachment zone in the root part. A width of the strips are attached to the root part, preferably the width is 1 mm that is more than 0.1 mm. This will make rolling of the device automated as one robot arm grab the urisheath and a hook grabs the handle providing resistance during rolling of the urisheath, whereby tangling of the strips is avoided.

For the injection moulding of a urisheath further comprising a handle portion, an injection moulding form further comprising a cavity for the handle portion is required. One example of such form is an injection moulding form wherein the cavity for the strip portion is located in longitudinal continuation of the cavity for the body portion and the cavity for the handle portion located to connect the strips.

In another embodiment, the handle is positioned above the tip portion, i.e. the strips extend from the root part in a direction towards the tip part. Such urisheath is injected moulded with an injection moulding form wherein the cavities for the strips terminate in a cavity for the handle above the tip portion. Having this handle in the centerline of the body portion enables that opening of the moulding forms will then reveal the strip portion.

In yet another embodiment, the handle is positioned beside the tip portion. Such urisheath is injected moulded with an injection moulding form wherein the cavity for the handle portion is sufficiently thick such that the cured material in this cavity can be pulled out (blown out). In one embodiment the cavity for the handle portion is thicker than the strip portion in general. An alternative injection moulding form comprises four parts: the forth part being between the two shield parts such that the cavity for the handle portion can be opened and the product removed from the cavity.

In one embodiment the handle it attached to the tip portion. This embodiment requires a subsequent dividing process. This can be carried out before rolling, after rolling, or even by the user.

It is preferred that the body portion is a silicone body portion.

To obtain the desired performance of the strip to un-roll the urisheath onto the penis, a strip material with sufficient release from the sheath adhesive has to be used. It is preferred that the strip is moulded in silicone.

The strip portion can be moulded in various hardness and types of silicone materials. In one embodiment the material is the same material, as the material used for the body portion. Particularly preferred for this is silicone C6-540 silicone from Dow Corning.

However, two-component injection moulding is feasible and enables attachment of the materials in liquid/non-vulcanised form. If 2-component moulding is used, it is preferred, that the strip is made in a harder silicone than the urisheath part. The preferred materials for the strip portion are platinum cured LSR silicones that give sufficiently release to the urisheath adhesive also after prolonged ageing. Particularly preferred is silicone C6-570 silicone from Dow Corning.

One aspect of the invention relates to a method for producing a urisheath comprising a body portion and a strip portion, comprising the steps of:
a) providing a moulding form for injection moulding;
b) injecting silicone into the form;
c) curing the silicone;
d) releasing the product from the moulding form;
e) rolling the urisheath to include the strips. During this operation the on side of the legs of the strips are twisted down on the surface of the sheaths to secure a rolling without wrinkles on the strip.

In the preparation of the rolled tubular section, the strips will typically be applied in the un-rolled condition. Thereafter, the tubular section is rolled, so that the strips are placed in between the inside and outside of the tube. Hereby, each of the strips forms a path along the tubular section.

In one embodiment, each of those paths is parallel to the longitudinal axis of the unrolled tubular section—hereby securing an even draw.

However, when placing the strips parallel to the longitudinal axis of the unrolled section, the rolled tubular section will have an un-even outer rim, thicker where the strips are, thinner at places along the rim, where the strips are absent. In order to obtain a smoother surface of the rolled tubular section, at least one path of the strip is a spiral shape.

The present invention also relates to a rolled urisheath comprising a body portion and a strip portion wherein the strip portion is attached to the body portion in an attachment zone.

The unrolling strip is considered to be a major benefit on the product, because that the application of the urisheath on the penis can be done by people with reduced hand function or by nurses wearing gloves. This unrolling strip also secures a smooth an easy unrolling of the product, giving improved security of leakage when wearing the product.

It is preferred that the thickness of the strip is about 0.06 mm. To secure flow of material through such thin product, the injection moulding form can be provided with more than one inlet ports.

Varying the thickness and the width can also vary the elastic feeling along the length of the strip. It is preferred to have rather large thickness of the handle part (e.g. 0.20 to 2.0 mm) and low thickness on the part alongside the shaft part (0.05 to 0.20 mm). This is in order to have a good rolling of the sheath.

Throughout the present specification, reference has been made to urisheath. However, the same technology can be used to injection mould a condom. Consequently, the present invention also relates to an injection moulding form for a condom and a condom semi-manufacture product.

EXAMPLES

Example 1

Double strip moulded almost separately from the urisheath only moulded together with the distant end of the urisheath.

This example requires large tooling and still leaves the strip not fully attached to the product.

Example 2

Strip moulded along sheath part of and attached by a thinner part that will be torn as the urisheath is unrolled. There can also be a perforation combined or instead of the thin part.

This example makes it easy to handle the urisheaths in the subsequent steps of the production. The difficult part here is to mould the combined handle function for the 2 legs of strip. The handle shall preferentially be of a length so that it ends before the end of the tip.

This can be done in several ways:

Either the tooling is made with more than 3 movable parts;
the tooling is made with 3 movable parts, but the strip (or strip handle) is attached to the tip of the urisheath, and shall be cut off in a following step;
the strip is made with 2 legs and the combined handle part is obtained by attaching these 2 legs to each other in a following step. They can be attached by mechanical or chemical means;
The combined handle part is made on top of the tip. However, this alternative gives an unrolling strip, which is longer than usually needed.

Example 3

To manufacture a urisheath we take a C6-540 (shore 40 A hardness) silicone from Dow Corning and injection into a mould, such that the thickness of the sheath portion is 0.20 mm and the strip portion is 0.10 mm in the lower part of the urisheath, and thickness of the sheath portion is 0.40 mm and the strip portion is 0.15 mm at the upper part of the urisheath close to the bellow part. The width of the strip is 8 mm along the length of the sheath part. The varying thickness of the strip provides for giving a not too elastic feeling when the user starts the unrolling with the strip. The thinner strip at the bottom secures that the strip is not giving a too high unevenness of the sheath portion in its rolled position, which possibly could give uneven unrolling and wrinkles of the sheath when unrolled by the user. The handle part of the strip is made in a thickness of e.g. 0.6 mm and shall secure a god grip also for people with reduced hand function.

Example 4

In another example the urisheath and the strip is made in two different silicones by two-component injection moulding. The sheath part is moulded as in example 1 in C6-540 silicone from Dow Corning. The strip part is made in C6-570 silicone from Dow Corning. This is a silicone of higher hardness (shore 70 A hardness). The strip part shall be made in a thickness of 0.06 mm at the lower part and a thickness of 0.10 mm at the upper part close to the bellow part. The width of the strip is still 8 mm along the length of the sheath part. The thinner strip reduces the possibility for uneven unrolling and wrinkles further compared to example 1, but is off cause also more complicated and costly to produce. The handle part of the strip is made in a thickness of e.g. 0.4 mm and shall secure a good grip also for people with reduced hand function.

FIGURES

Further advantages of the present invention will be understood in the following detailed description wherein the invention will be described with reference to the enclosed figures. The figures and detailed description serves as examples only and should not be understood as limiting the scope of the invention.

Figure 8:
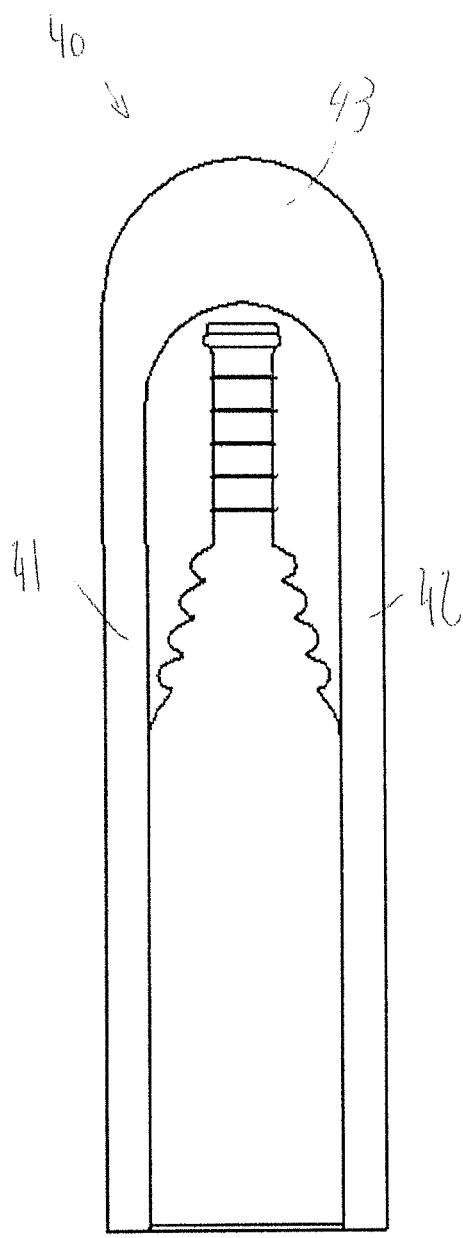
Figure 9:
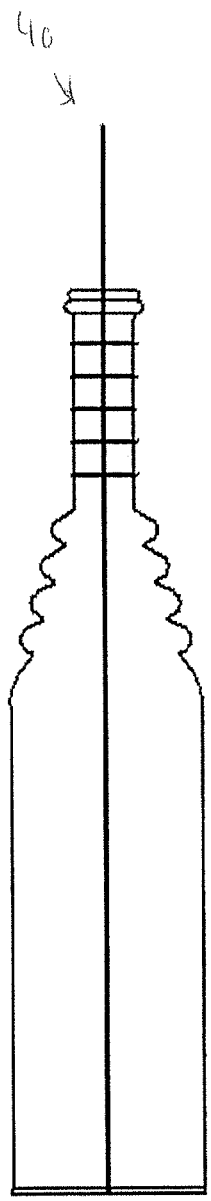
Figure 10:
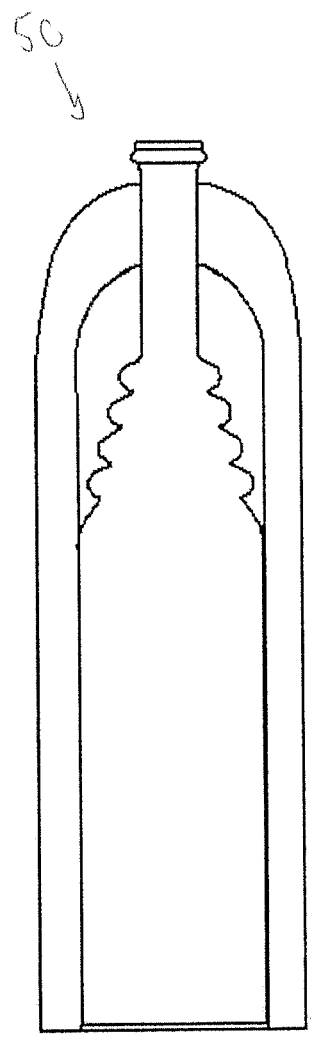
Figure 11:
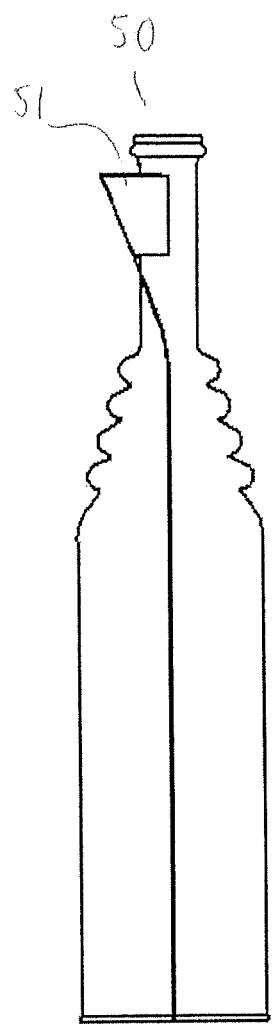

FIGS. 1 and 2 illustrate a first embodiment of the invention seen from the side in two different angles, FIGS. 3, 4 and 5 illustrates a second embodiment of the invention seen from the side in two different angles and in perspective from above, FIGS. 6 and 7 illustrates a third embodiment of the invention seen from the side in two different angles, FIGS. 8 and 9 illustrates a fourth embodiment of the invention seen from the side in two different angles, and FIGS. 10 and 11 illustrates a third embodiment of the invention seen from the side in two different angles.

FIGS. 1 and 2 shows one embodiment of an injection moulded semi-manufactured urisheath assembly 1 according to the invention.

An urisheath 2 and a strip portion 3 form the urisheath assembly 1.

The urisheath consist of a tip part 4, a shoulder part 5 and a body part 6.

The tip part 4 extends in distance A from the shoulder part 5 towards an outlet end 9 and is adapted to be connected to a discharge tube (not shown). A drainage tube 7 whereon five round going friction ribs 8 are formed makes up the tip part. The ribs provide frictional means so that a user, e.g. the patient or nurse, can control the drainage tube without loosing the grip. At the outlet end 9 of the drainage tube there is provided a protruding connection rib 10. This connection rib protrudes further outwards in a radial distance from the drainage tube than the round going friction ribs 8. The connection rib function provides frictional engagement when the drainage tube and the discharge tube are connected.

The shoulder part 5 connects the body part to the tip part. In the present embodiment the shoulder part is formed with four round going bulbous rings 11.

The body part 6 is formed as a tubular section extending from the shoulder part to a mounting opening 12. The body part is divided into a root portion 13, which extends in a distance B from the mounting opening 12 towards the outlet end 9 and a centred part 14 extending in a distance C from the root portion 13 towards the outlet end 9.

The strip portion 3 is formed as two parallel strips 14,15 extending from the mounting opening 12 towards the outlet end 9, terminating approximately at the beginning of the tip part. A handle 16 in the shape of an arc formed bridge strip connects the ends of the two strips closest to the outlet end. The strip portion 3 is releasable attached to the urisheath via the respective sides, facing toward the urisheath, of the two parallel strips which extends along the body part by longitudinal attachment zones 14', 15'.

The attachment zones are typically formed as weakened zones, i.e. having lower tear strength than the strip portion 3 and the urisheath 2 respectively. During injection moulding these attachment zones may be provided in a number of different ways. For example it may be provided as a decrease in the thickness of the material compared to the thickness of the parallel strips and/or the thickness of the wall of the body part. Alternatively they may be provided as two lines of perforations extending along the body part or as a few, for example one or two, connection points between the parallel strips and the urisheath.

Thus when the urisheath is held in a fixed position and the strip portion is pulled the urisheath assembly will be separated along the attachment zones.

Furthermore, as can be seen in FIG. 2 the strip portion is formed with a bend 17. This allows the strip portion to have length with is shorter than the extent of the urisheath, while at the same time connecting the two parallel strips 14 and 15 with a continuous handle 16 as the handle is guided around the tip part 4.

FIGS. 3, 4 and 5 show an alternative embodiment injection moulded semi-manufactured urisheath assembly 20 according to the invention.

In this embodiment the urisheath is the same as in FIGS. 1 and 2, however, the strip portion is formed as two individual strips 21 and 22. The two individual strips are connectable via connection ends 23 and 24 which are formed with locking means in form of a through going hole 25 provided in the first connection end and a tab 26 on the second connection end 24. When used the tab is pushed into the through going hole locking the two connection ends together thereby forming a handle (the handle not shown assembled).

During injection moulding the strip portion is attached to the urisheath in a similar way as described with respect to FIGS. 1 and 2.

FIGS. 6 and 7 shows yet another embodiment injection moulded semi-manufactured urisheath assembly 30 according to the invention.

The strip portion 3 and the urisheath 2 correspond to the part as described in FIGS. 1 and 2, however, during injection moulding they have been assembled differently.

The strip portion 3 is attached to the urisheath 2 at attachment points 31 and 32 at the root portion of the urisheath and extends in a direction from the root portion and away from the outlet end 9 of the urisheath.

Yet another embodiment of an injection moulded semi-manufactured urisheath assembly 40 according to the invention is shown in FIGS. 8 and 9. In this embodiment the parallel strips 41 and 42 extends from the root portion of the urisheath almost to the outlet end of the tip part. Thus it is not necessary to provided the parallel strip with a bend, such as described in FIGS. 1 and 2, as the handle 43 connecting the two parallel strips is arranged past the tip part.

In a further embodiment of an injection moulded semi-manufactured urisheath assembly 50 according to the invention is shown in FIGS. 10 and 11. This embodiment is almost identical to the one shown in FIGS. 1 and 2 except that tabs 51 and 52 (tab 52 is not seen in the drawing as the tab 51 covers it) connects the handle 16 and the tip part 4. These tabs results of the injection moulding process as they are created in order to provided and even distribution and even flow and curing of the urisheath assembly material during production. Tabs 51 and 52 will often be cut away before selling the product.

The invention claimed is:

1. A urisheath comprising:
a body portion defining a through lumen, said body portion comprising a root part provided at an inlet end, a centered part, and a tip part;
a connection part provided at an outlet end of the tip part, adapted for attachment to a drain tube; and
a strip portion, said strip portion comprising at least two elongated individual strips, including at least one first elongated individual strip connected at a proximal end thereof to one of said root part and said centered part, and a second elongated individual strip connected at a proximal end thereof to one of said root part and said centered part, wherein a distal end of said at least one first elongated individual strip includes an aperture defined therein, and a distal end of said at least one second elongated individual strip includes a tab portion adapted to be inserted into said aperture, thereby at least temporarily locking said at least one first elongated individual strip and said at least one second elongated individual strip together to define at least one handle.

2. A urisheath comprising a body portion, said body portion comprising a root part, a centered part, and a tip part, and a strip portion, said strip portion comprising at least two elongated individual strips, including at least one first elongated individual strip connected at a proximal end thereof to one of said root part and said centered part, and at least one second elongated individual strip connected at a proximal end thereof to one of said root part and said centered part, wherein a distal end of said at least one first elongated individual strip is adapted to at least temporarily attach to a distal end of said at least one second elongated individual strip to define at least one handle.

3. The urisheath according to claim 2, wherein said strip portion is attached to said body portion in an attachment zone, said attachment zone including at least one weakened zone.

4. The urisheath according to claim 1, wherein said strip portion is attached to said body portion along said entire centered part.

5. The urisheath according to claim 1, further comprising an attachment zone attaching said strip portion to said body portion, wherein the attachment zone has a lower tear strength than said body portion and said tip part.

6. The urisheath according to claim 2, wherein said first and second elongated strips temporarily attach together to define said handle with connecting means defined on each of said elongated strips.

7. The urisheath according to claim 2, wherein said handle is positioned below said body portion, and wherein said at least one first and second elongated individual strips extend from said root part in a direction away from said tip part.

8. The urisheath according to claim 2, wherein said handle is positioned above said tip part, and wherein said at least one first and second elongated individual strips extend from said root part in a direction towards said tip part.

9. The urisheath according to claim 2, wherein said handle is positioned beside said tip part.

10. The urisheath according to claim 2, wherein said handle is attached to said tip part.

11. The urisheath according to claim 1, wherein said body portion comprises a silicone body portion.

12. The urisheath according to claim 1, wherein said strip portion comprises a silicone strip portion.

13. A rolled urisheath comprising a body portion, said body portion defining a through lumen configured to receive a liquid and comprising a root part, a centered part and a tip part, wherein said tip part comprises a connection part configured to attach to a drain tube to drain the liquid away from the urisheath, and a strip portion attached to said body portion in an attachment zone, said strip portion comprising at least two elongated individual strips, including at least one first elongated individual strip connected at a proximal end thereof to one of said root part and said centered part, and at least one second elongated individual strip connected at a proximal end thereof to one of said root part and said centered part, wherein a distal end of said at least one first elongated individual strip includes a tab portion adapted to at least temporarily attach to an aperture defined in a distal end of said at least one second elongated individual strip, to define at least one handle.

14. The rolled urisheath according to claim 13, wherein the attachment zone comprises at least one weakened zone having a lower tear strength than tear strengths of said strip portion and said body portion respectively.

15. The rolled urisheath according to claim 14, wherein the weakened zone is formed of the same material as said strip portion and said body portion, and has a smaller thickness than said strip portion and said body portion.

16. The urisheath according to claim 13, wherein said strip portion is attached to said body portion along the entire centered part.

17. The rolled urisheath according to claim 13, wherein the attachment zone has a lower tear strength than said body portion and the tip part.

18. The rolled urisheath according to claim 13, wherein said handle is positioned below said body portion, and wherein said at least one first and second elongated individual strips extend from said root part in a direction away from said tip part.

19. The rolled urisheath according to claim 13, wherein said handle is positioned above said body portion, and wherein said at least one first and second elongated individual strips extend from said root part in a direction towards said tip part.

20. The rolled urisheath according to claim 13, wherein said body portion comprises a silicone body portion.

21. The rolled urisheath according to claim 20, wherein said strip portion comprises a silicone strip portion.

22. A rolled urisheath comprising a body portion, said body portion comprising a root part, a centered part, and a tip part adapted to attach to a drain tube, and a strip portion, wherein the strip portion is attached to said body portion in an attachment zone, wherein the attachment zone comprises at least one weakened zone having a lower tear strength than said strip portion and said body portion respectively, and wherein said strip portion comprises at least two elongated individual strips, including at least one first elongated individual strip connected at a proximal end thereof to one of said root part and said centered part, and at least one second elongated individual strip connected at a proximal end thereof to one of said root part and said centered part, wherein a distal end of said at least one first elongated individual strip includes at least one tab portion insertable at least temporarily into an aperture defined in a distal end of said at least one second elongated individual strip to define at least one handle.

23. A rolled urisheath comprising a body portion, said body portion comprising a root part, a centered part, and a tip part adapted to attach to a drain tube, and a strip portion, wherein the strip portion is attached to the body portion in an attachment zone, wherein said attachment zone comprises a weakened zone formed of the same material as said strip portion and said body portion, and has a smaller thickness than said body portion, and wherein the strip portion comprises at least two elongated individual strips, including at least one first elongated individual strip connected at a proximal end thereof to at least one of said root part and said centered part, and at least one second elongated individual strip connected at a proximal end thereof to one of said root part and said centered part, wherein a distal end of said at least one first elongated individual strip is adapted to at least temporarily attach to a distal end of said at least one second elongated individual strip to define at least one handle by a temporary connection of at least one tab defined on at least one of said elongated individual strips with at least one aperture defined on at least one other of said elongated individual strips.

24. A rolled urisheath comprising a body portion, said body portion comprising a root part, a centered part, and a tip part adapted to attach to a drain tube, and a strip portion, wherein the strip portion comprises at least two elongated individual strips, including at least one first elongated individual strip connected at a proximal end thereof to one of said root part and said centered part, and at least one second elongated individual strip connected at a proximal end thereof to one of said root part and said centered part, wherein a distal end of said at least one first elongated individual strip includes at least one tab insertable into at least one aperture defined in a distal end of said at least one second elongated individual strip to define at least one handle.

25. A urisheath according to claim 1, further comprising a connection part, adapted to connect a drain tube to said tip part of said body portion, wherein said connection part has a radial dimension larger than a radial dimension of said tip part.

26. A rolled urisheath according to claim 13, wherein said connection part has a radial dimension larger than a radial dimension of said tip part.

27. A urisheath comprising a body portion, said body portion defining a through lumen, comprising a root part, a centered part, and a tip part, said tip part including a connection part adapted to attach to a drain tube to drain liquid away from the urisheath, the connection part having a radial dimension larger than a radial dimension of said tip part, and a strip portion attached to said body portion in an attachment zone, the attachment zone including a weakened zone with a lower tear strength than said strip portion and said body portion respectively, and wherein said strip portion comprises at least two elongated individual strips, including at least one first elongated individual strip connected at a proximal end thereof to one of said root part and said centered part, and at least one second elongated individual strip connected at a proximal end thereof to one of said root part and said centered part, wherein a distal end of said at least one first elongated individual strip includes at least one tab insertable into at least one aperture defined in a distal end of said at least one second elongated individual strip to define at least one handle.

28. A urisheath according to claim 27, wherein the weakened zone has a smaller thickness than said body portion.

* * * * *